(12) United States Patent
Shulman et al.

(10) Patent No.: US 8,993,639 B2
(45) Date of Patent: Mar. 31, 2015

(54) COMPOUND AND METHOD FOR TREATMENT OF GASTROESOPHAGEAL REFLUX

(76) Inventors: Burt Shulman, Wappingers Falls, NY (US); Barrie R. Froseth, Plymouth, MN (US); Ravindranath S. Menon, Rogers, MN (US)

( * ) Notice: Subject to any disclaimer, the term of this patent is extended or adjusted under 35 U.S.C. 154(b) by 181 days.

(21) Appl. No.: 12/933,440

(22) PCT Filed: Mar. 20, 2009

(86) PCT No.: PCT/US2009/001789
§ 371 (c)(1),
(2), (4) Date: Nov. 19, 2010

(87) PCT Pub. No.: WO2009/117160
PCT Pub. Date: Sep. 24, 2009

(65) Prior Publication Data
US 2011/0076252 A1    Mar. 31, 2011

Related U.S. Application Data

(60) Provisional application No. 61/070,208, filed on Mar. 20, 2008.

(51) Int. Cl.
| | |
|---|---|
| *A01N 33/18* | (2006.01) |
| *A01N 33/24* | (2006.01) |
| *A01N 31/04* | (2006.01) |
| *A01N 61/00* | (2006.01) |
| *A61K 31/00* | (2006.01) |
| *A61K 31/198* | (2006.01) |

(52) U.S. Cl.
CPC ................................ *A61K 31/198* (2013.01)
USPC .............................................. 514/740; 514/1

(58) Field of Classification Search
None
See application file for complete search history.

(56) References Cited

U.S. PATENT DOCUMENTS

| | | | |
|---|---|---|---|
| 6,117,908 A | 9/2000 | Andrews et al. | |
| 6,831,103 B1 | 12/2004 | Ueda et al. | |
| 8,097,286 B2* | 1/2012 | Samuel et al. | 424/725 |
| 2008/0009505 A1 | 1/2008 | Hodges et al. | |
| 2009/0047405 A1 | 2/2009 | Zhang | |

FOREIGN PATENT DOCUMENTS

WO    WO 96/00680    4/1996

OTHER PUBLICATIONS http://signsandsymptoms360.com/arthritis-prevention-do-these-things-and-prevent-arthritis.html, Arthritis Prevention: Do These Things and Prevent Arthritis, printed Aug. 26, 2012, author unknown, no journal, no number, no volume, no pages, total of 8 pages.*
Terri Mitchell (Jan. 2006) "Natural Support for Sleep, Mood, and Weight", Life Extension Magazine, Found online at https://www.lef.org/magazine/mag2006/jan2006_report_theanine_01.htm, 6 pages long, no page numbers, volume, or issue number.*
James Heffley (Jul. 4, 2003) "To Your Health: I sometimes feel calmer after drinking green tea despite its caffeine content. Could it be the theanine in the tea?", found online at http://www.austinchronicle.com/columns/2003-07-04/166635/, no volume or issue number, 3 pages long.*
Cantu, et al. (2003) "Effect of non-selective [gamma]-aminobutyric acid receptor stimulation on motor function of the lower oesophageal sphincter and gastro-oesophageal reflux in healthy human subjects", Aliment. Pharmacol. Ther., 18(7): 699-704.*
Lidums, et al. (2000) "Control of Transient Lower Esophageal Sphincter Relaxations and Reflux by the GABAB Agonist Baclofen in Normal Subjects", Gastroenterology, 118: 7-13.*
Hart, "Heartburn—is Glutamine a cure?" http://ezinearticles.com/?Heartburn---Is-Glutamine-a-Cure?&id=540785 (downloaded 2007).
Hornby et al., "Central Mechanisms of Lower Esophageal Spincter Control." Gastroenterol. Clin. North. Am., Dec. 2002; 31(4 Suppl):S11-20.
Meining et al, "Lower Esophageal Sphincter Pressure in Patients with Gastroesophageal Reflux Diseases and Posture and Time Patterns." Disease of the Esophagus. 2004; 17(2):155-8.
Nathan, et al., "The Neuropharmacology of L-Theanine (N-Ethyl-L-Glutamine): A Possible Neuroprotective and Cognitive Enhancing Agent." Journal of Herbal Pharmacotherapy, 2006; 6(2):21-30.
HTTP://www.vivani-chocolate.de/P_USA_Bitter-Greentea.html (downloaded May 16, 2014).
HTTP://users.bestweb.net/~om/~kombu/konnection/reflux.html (downloaded May 16, 2014).
PCT/US2009/001789 International Search Report dated Apr. 22, 2010.
PCT/US2009/001789 International Preliminary Report on Patentability dated Sep. 21, 2010.
PCT/US2009/001789 Written Opinion dated Feb. 2, 2010.
Beaumont, H., et al., "The role of $GABA_A$ receptors in the control of transient lower oesophageal sphincter relaxations in the dog." British Journal of Pharmacology, Mar. 2008; 153(6):1195-1202.
Egashira, N., et al., "Involvement of $GABA_A$ receptors in the neuroprotective effect of theanine on focal cerebral ischemia in mice." J. Pharmacol. Sci. Oct. 2007; 105(2): 211-214.

* cited by examiner

*Primary Examiner* — Robert M Kelly

(57) ABSTRACT

The invention relates to the use of a L-theanine for the treatment of gastroesophageal reflux disease (e.g., heartburn) in a human or animal, including useful methods and compositions.

21 Claims, No Drawings

COMPOUND AND METHOD FOR TREATMENT OF GASTROESOPHAGEAL REFLUX

PRIORITY DATA

The present application claims benefit from International Application No. PCT/US2009/001789, which was filed on Mar. 20, 2009, which in turn claims priority to U.S. Provisional Application No. 61/070,208, filed Mar. 20, 2008, and titled "Compound And Method for Treatment of Gastroesophageal Reflux", the entire contents of both applications being incorporated herein by reference in their entireties.

FIELD OF THE INVENTION

The invention relates to the use of a L-theanine for the treatment of gastroesophageal reflux disease (e.g., heartburn) in a human or animal, including useful methods and compositions.

BACKGROUND

The amino acid, L-theanine (N-ethyl-Lgluatmine, or theanine) is a major amino acid uniquely found in green tea. This compound has several physiological effects. L-Theanine is known, for instance, for having anti-anxiety effects in humans and animals. L-Theanine is also believed to act as a GABA agonist after being ingested (P. J. Nathan, et al., J. Herb. Pharmacother., 2006; 6(2):21-30). GABA (4-aminobutanoic acid, or γ-aminobutyric acid) is an endogenous neurotransmitter in the central and peripheral nervous systems.

Gastro-esophageal reflux disease (GERD) is an upper gastroesophageal tract disease. Certain useful therapies have been directed toward reducing gastric acid secretion, such as by use of a gastric acid inhibitor such as either a proton pump inhibitor or a histamine H(2)-receptor blocker (H(2)-blocker), or by otherwise lowering pH in the stomach such as by use of an antacid. GERD is believed to be a result of periodic lower esophageal sphincter relaxations (PLESR, or TLERS ("transient lower esophageal sphincter relaxations")), and/or generalized diminished lower esophageal sphincter tone (A. Meining et al, Dis Esophagus 2004; 17(2): 155-8). It has been shown that increasing GABA receptor activity, increases lower esophageal sphincter tone and reduces lower esophageal sphincter relaxations (P. J. Hornby et al., Gastroenterol. Clin. North. Am., 2002 December; 31(4 Suppl):S11-20, v-vi).

U.S. Pat. No. 6,117,908 describes that receptors for GABA have traditionally been divided into $GABA_A$ and $GABA_B$ receptor subtypes. $GABA_B$ receptors belong to the superfamily of G-protein coupled receptors. $GABA_B$ receptor agonists are described as being of useful in the treatment of CNS disorders such as muscle relaxation in spinal spasticity, cardiovascular disorders, asthma, gut motility disorders such as irritable bowel syndrome, and as prokinetic and anti-tussive agents. $GABA_B$ receptor agonists have also been disclosed as useful in the treatment of emesis (WO 96/11680), and as reflux inhibitors (U.S. Pat. No. 6,117,908). This latter patent document includes a description of the $GABA_B$ agonist baclofen, among other compounds, as potentially useful reflux inhibitors.

The citations above, shall not be construed as an admission that such reference is available as prior art to the present invention.

SUMMARY OF THE INVENTION

It has now been discovered that a certain compound that exhibits the physiological property of increasing neuronal GABA activity, has the utility of ameliorating gastroesophageal reflux in the human. This compound is an amino acid enzymatically derived from green tea and is know as L-theanine and has a chemical structure, γ-ethylamino-L-glutamic acid.

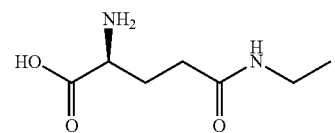

The invention constitutes a new use for L-Theanine when introduced into a person or animal. Administering theanine can increase neuronal GABA activity, inhibit lower esophageal sphincter relaxations, and thereby relieve gastroesophageal reflux or its symptoms. The dosage can be any useful amount, such as from 50 to 600 milligrams per day. The dosage can be varied based on the severity of symptoms, and higher or lower dosages can be useful. The dosage can be delivered as often as is useful, optionally regularly, such as once a day, twice a day, or three times a day, to provide a total dosage that will be useful to relieve gastroesophageal reflux or its symptoms. For example an oral dosage of from 100 to 200 milligrams theanine may be administered up to three times a day, for a total of from 300 to 600 milligrams theanine per day.

By these and other useful methods, embodiments of the invention provide for the treatment of gastroesophageal reflux or symptoms thereof, including heartburn, by administering L-theanine, e.g., by oral administration. The amount may be a gastroesophageal reflux ameliorating effective amount. An alternate amount may be an amount to treat or alleviate a symptom of gastroesophageal reflux such as heartburn, e.g., a heartburn ameliorating effective amount. The dose can be administered on a periodic basis for the continuous amelioration of gastroesophageal reflux in humans. Non-oral administration can also be useful, e.g., by injection or transdermally, in gastroesophageal reflux ameliorating effective amounts.

The invention also relates to novel dosage forms that contain theanine, such as in the form of a food product, a dietary supplement, a drug, an over-the-counter drug, or other ingestible dosage form. Certain exemplary dosage forms in the form of a dietary supplement, pharmaceutical, or drug, may be an "oral dosage form" that may be in the form of a tablet, capsule, caplet, etc., containing theanine. These or other oral dosage forms (e.g., food products) can alternately take the form of an aqueous solution, suspension, or mixture, optionally prepared from a solid (e.g., powder, granules, or other particles that can become dissolved or suspended in a liquid) or liquid concentrate just prior to ingestion. Dosage forms in the form of food products may be any form of food, such as a candy, gum, baked good, liquid beverage, cereal, bar, dessert, etc., as described. The amount of theanine in a dosage form may be useful to provide a desired dosage on a per dose basis or on a daily dosage basis.

In one aspect the invention relates to a method of treating gastroesophageal reflux disease, or a symptom thereof. The method includes administering theanine in an effective amount.

In another aspect the invention relates to a dosage form for treating gastroesophageal reflux disease. The dosage form includes theanine in an effective amount, such as a gastroesophageal reflux-inhibiting amount.

In yet another aspect the invention relates to a dosage form for treating heartburn. The dosage form includes theanine in an effective amount, such as a heartburn-inhibiting amount.

DETAILED DESCRIPTION OF THE INVENTION

The invention provides a compound, L-theanine (or "theanine"), and method of treatment, using this compound, for the treatment of human gastroesophageal reflux. The compound theanine is commercially available as a derivative of green tea. It is obtainable as a high purity, white crystalline powder that readily dissolves in water.

Exemplary methods of the invention involve administering an effective dose of theanine to a person (human) or animal. This effective dose is preferably administered orally, but may be administered in other forms, such as by injection, transdermally, etc. Examples of effective doses can be in the range from 50 to 200 milligrams, e.g., 100-200 milligrams (mg) per dose. Other dosages are also useful depending on factors such as the severity of the symptoms of gastroesophageal reflux. Doses may be taken once or multiple times daily, over a length of days or weeks, or longer. An example of a total daily dose may be from 50 to 600 milligrams; e.g., from 300 to 600 milligrams total theanine taken in a single day (e.g., at intervals of approximately eight hours), by taking three separate doses of from 100 to 200 milligrams theanine.

A treatment regime may include different total daily amounts, or different amounts of a single dosage, depending on factors such as severity of symptoms, length of treatment, and patient weight.

As an exemplary regime for a human patient with moderate to severe GERD symptoms, a treatment regime may include multiple days or weeks of taking from 300 to 600 milligrams theanine per day, such as doses of 100 to 200 mg theanine three times per day. If symptoms are reduced, treatment may be suspended or the total daily dosage may be reduced, for example after two days, after one week, or after two weeks, the total daily dosage may be reduced to a daily dose in the range from 50 to 200 mg theanine. Optionally, during any period of the treatment, a supplemental dosage of from 20 to 200 mg theanine may be taken prior to a precipitating factor for gastro-esophageal reflux such as ingestion of food or recumbency for resting or for overnight sleep.

An exemplary regime for a human patient with minor to moderate symptoms, such as heartburn symptoms, may include multiple days of taking from 300 to 600 milligrams theanine per day, such as doses of 100 to 200 mg theanine three times per day for two, three, four, or five days. If symptoms are reduced, treatment may be suspended or the dosage may be reduced, such as after two days, after one week, or after two weeks, the total daily dosage may be reduced to a daily dose in the range from 50 to 200 mg theanine. Optionally during any period of the treatment a supplemental dosage of from 20 to 200 mg theanine may be taken prior to a precipitating factor for gastro-esophageal reflux such as ingestion of food or recumbency for resting or for overnight sleep.

Normally there is a period of time between ingestion of theanine and a subsequent physiological effect of increasing GABA activity. Thus, according to the above, or alternate, treatment regimes, an initial dose can optionally be administered substantially before ingestion of food (e.g., 2 to 4 hours), which is the typical precipitating factor for gastroesophageal reflux. Once the initial dosage is administered subsequent doses may be administered approximately one half hour before a meal. Another typical precipitating factor for gastroesophageal reflux is recumbency, either after a meal or for resting or sleeping. A dose may thus be administered before lying down.

A dose may be modulated to suit an individual's physiology and environment, in that the least amount of treatment material is used to avoid symptoms of gastroesophageal reflux. Additionally, certain foods are known precipitators of gastroesophageal reflux, such as, chocolate and coffee, and the individual may increase his usual dosage by a factor of two in order to avoid symptoms when these factors are present.

A method as described may be performed by administering any of various useful dosage forms, as described, e.g., including a dosage form that is a food product, a dietary supplement, a pharmaceutical or drug.

Certain exemplary dosage forms in the form of a dietary supplement, pharmaceutical, or drug, may be an oral delivery means or an "oral dosage form" that may be in the form of a tablet, capsule, caplet, etc., containing theanine. These or other oral dosage forms (e.g., food products) can alternately take the form of an aqueous solution, suspension, or mixture, optionally prepared from a solid (e.g., powder, granules, or other particles that can become dissolved or suspended in a liquid) or liquid concentrate just prior to ingestion. Dosage forms in the form of food products may be any form of food, such as a candy, gum, baked good, liquid beverage, cereal, bar, dessert, etc., as described. Optionally, by any oral dosage form, theanine may be administered orally using a time released dosage form or any combination of the above or other delivery means.

As used herein, the term an "oral dosage form" refers to any sort of suitable dosage form used to deliver theanine as described herein, to a subject human or animal. Preferred formulations are oral dosage forms. However, other formulations, for example, formulations for injection (e.g., subcutaneous, intramuscular, etc.), formulations for topical application, or formulations for rectal, nasal, or optical administration are contemplated and can be prepared and administered to a subject. An oral dosage form includes any liquid composition, solid composition, solid composition that can be dissolved or suspended in a liquid, or combination liquid and solid composition that can be suitable delivered to a subject. Exemplary oral dosage forms include solid dosage forms, for example, tablets, capsules, including soft elastic capsules or hard elastic capsules having a solid or liquid fill, lozenges, candies, chewable tablets or chewable capsules, baked goods, liquid beverages, and other liquid dosage forms, for example, solutions, suspensions, dispersions, or syrups, and solids that may be dissolved or suspended in a liquid.

A dosage form can include additional active and inactive ingredients, including, but not limited to surfactants, cosolvents, excipients, food ingredients, nutrients, microbes, yeasts, fillers. Certain dosage forms such as tablets and capsules can optionally include solvents or cosolvents such as alcohols and polyols, polyethylene glycols ethers, amides, esters, other suitable cosolvents, and mixtures thereof. A dosage form can also include excipients or additives such as sweeteners, flavorants, colorants, antioxidants, preservatives, chelating agents, viscomodulators, tonicifiers, odorants, opacifiers, suspending agents, binders, other food ingredients, vitamins, minerals, and mixtures thereof, as will be apparent from the overall disclosure herein.

A "dietary supplement," also known as a "food supplement" or a "nutritional supplement," is generally a preparation intended to provide nutrients, such as vitamins, minerals, fatty acids or amino acids, fiber, carbohydrates, or protein, that are missing or are not consumed in sufficient quantity in a person's diet. Typically a dietary supplement can include one of these types of nutrients in a concentrated amount, which is an amount that is higher than amounts naturally or typically included in a non-fortified food product; also typically, the form of the dietary supplement can be designed for convenience, such as being in the form of a concentrated liquid or a tablet, capsule, or caplet. According to the present disclosure, a dietary supplement can include theanine in an amount as described, or otherwise an amount for use according to the methods described. A dietary supplement is a product available on a non-prescription basis, is not considered to be a "food product," and may include theanine alone or in combination with other vitamins, minerals, sweeteners, flavorants, food ingredients, etc., as described. A working definition useful to define a "dietary supplement" for purposes of the present description, can be the definition of the United States Food and Drug Administration, in the Dietary Supplement Health and Education Act of 1994, defining a "dietary supplement" as: a product (other than tobacco) that is intended to supplement the diet that bears or contains one or more of the following dietary ingredients: a vitamin, a mineral, an herb or other botanical, an amino acid, a dietary substance for use by man to supplement the diet by increasing the total daily intake, or a concentrate, metabolite, constituent, extract, or combinations of these ingredients; is intended for ingestion in pill, capsule, tablet, or liquid form; is not represented for use as a conventional food or as the sole item of a meal or diet; is labeled as a "dietary supplement." Probiotic dosage forms, prebiotic dosage forms, and "medical foods," as described herein, containing theanine, can be considered dietary supplements.

The terms "drug" ("pharmaceutical") for purposes of the present description are used in a manner consistent with the meaning of the term "drug" at the United States Federal Drug and Cosmetic Act, which defines the term "drug" as meaning: (A) articles recognized in the official United States Pharmacopoeia, official Homoeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals; and (D) articles intended for use as a component of any article specified in clause (A), (B), or (C). A "drug" (also "pharmaceutical") dosage form according to the present invention can be a dosage form that contains theanine as an active ingredient, optionally in a time-release form, in an amount as described herein and useful according to a described method.

The term "over-the-counter drug" as contemplated by the present description is consistent with USFDA regulations, which consider an over-the-counter drug to be safe and effective for use by the general public without a doctor's prescription.

A dosage form may alternately be a "food product," which is a food that includes theanine incorporated into the food as an ingredient, in an amount as described herein, with other conventional food ingredients, for human or animal consumption. A "food product" does not generally refer to a consumable item referred to as a dietary supplement, a pharmaceutical, or a drug, although a food product may optionally include added vitamins, minerals, amino acids, and the like, in fortifying amounts. A "fortifying amount" of a vitamin, mineral, or amino acid, is an amount that would not be naturally found in a food product of a particular type in the absence of ingredients added to specifically increase the amount of vitamin, mineral, or amino acid.

Examples of dosage forms in the form of a food product can include baked goods, for example, bread, wafers, cookies, crackers, pretzels, pizza, and rolls; ready-to-eat breakfast cereals, breakfast pastries, hot cereals; pasta products; dough products; snacks such as fruit snacks, pudding; spreads, salty snacks, grain snacks, microwave popcorn; dairy products such as yoghurt, cheese, butter or butter substitutes, and ice cream; sweet goods such as hard candy, soft candy, and chocolate; beverages; animal feed, pet foods such as dog food and cat food, aqua-culture foods such as fish food and shrimp feed; and special purpose foods such as baby food, infant formulas, hospital food; sports food; performance food; nutritional bars; nutritional beverage; a fortified food; food preblends or mixes for home or food service use such as preblends for soups or gravy, dessert mixes, dinner mixes, liquid beverages, baking mixes such as bread mixes, and cake mixes; baking flour, starch, protein, a protein ingredient, or other food ingredients; and dissolvable or suspendable solids. A food product dosage form may be sold and packaged for consumption as a single serving, or multiple servings may be contained in a package.

The size of a food product or a serving of a food product can be any useful size. Based on mass an exemplary serving of a food product dosage form may be from 30 to 60 grams to 750 grams, e.g., from 50 to 500 grams. Based on volume a serving may be from 1 or 2 ounces to 24 ounces (30 or 60 to 710 milliliters), e.g., from 8 to 18 ounces (237 to 523 milliliters). A serving may include from 50 to 200 milligrams theanine, e.g., from 100 to 200 milligrams theanine. A product may be sold in an amount that contains multiple servings, e.g. 2, 4, 6, or 8 servings, and may then include a corresponding multiple amount of a single dosage of theanine.

A food product in the form of a liquid food product or "liquid beverage" may be a dairy product such as milk, a grain beverage such as soy milk or rice milk, tea, coffee, or a shake or malt product optionally including protein. Generally, this includes some form of food flavoring (sweetener (natural or synthetic), salt, dairy, fruit juice, coffee, tea, etc.), and additionally according to the present description will include an amount of theanine as described. A liquid beverage may also include additional fortifying amounts of nutritional ingredients such as protein, amino acids, vitamins, and minerals, in the form of a "sport drink" or a "nutrition drink."

As more specific examples, a liquid beverage dosage form can be in the form of a breakfast drink such as orange juice, grape juice, apple juice, lemonade, or other fruit juices; tea, green tea, coffee, soup, or a chocolate drink; a liquid made by mixing a solid powder into a liquid such as water or milk; etc. Another specific example can be a nutritional beverage, meaning a any of these that includes theanine and one or more additional vitamin, mineral, amino acid, etc., found in a fortifying amount.

An exemplary serving size for a liquid beverage can be from 1 to 3 cups and a serving may include from 50 to 200 milligrams theanine, e.g., from 100 to 200 milligrams theanine. Alternate liquid beverage dosage form may be of a size (volume) in the range from 5 to 24 fluid ounces and a serving may include from 50 to 200 milligrams theanine, e.g., from 100 to 200 milligrams theanine.

An alternate dosage form may be a dissolvable tablet (e.g., a hard or soft candy, a mint, or a lozenge). A dissolvable tablet dosage form may optionally contain natural or artificial sweetener or flavorant such as fruit juice, chocolate, mint, caramel, etc. The dosage form may be sold as a package of individually wrapped pieces, or in a roll form and may be of a mass in the range from about 1 gram to 5 grams, e.g., from 1 to 3 grams.

Similarly, a dosage form may be a piece of gum containing theanine. A serving size may be, e.g., from 5 to 30 grams. The dosage form may contain a gum base and may optionally contain natural or artificial sweetener or flavorant such as fruit juice, chocolate, mint, caramel, etc. The dosage form may be sold as a package of individually wrapped pieces such as sticks and may be of a mass in the range from about 1 gram to 5 grams, e.g., from 1 to 3 grams.

A dosage form may be designed for consumption during breakfast, in the form of a breakfast cereal, yogurt, or baked good such as a cracker, wafer, or cookie.

A "medical food" generally is dietary food (this type of dosage form can be considered to be within the category of "dietary supplement" for purposes of the present description). A medical food can be specially formulated and intended for the dietary management of a disease that has distinctive nutritional need that cannot be met by normal diet alone, e.g., a defined in the Food and Drug Administration's 1988 Orphan Drug Act Amendments. Medical foods are distinct from the broader category of food products, nutritional supplements, pharmaceuticals, and drugs.

A "probiotic" or "probiotic material" is a dietary supplement that includes live bacteria or yeasts thought to be healthy for the host organism. According to the currently adopted definition by FAO/WHO, probiotics are live microorganisms that when administered in adequate amounts confer a health benefit on the host. A probiotic bacterial culture can be intended to assist the body's naturally occurring gut flora, an ecology of microbes, to re-establish themselves. Ingesting probiotic material may be useful after a course of antibiotics or as part of the treatment for gut-related candidiasis. In these cases, the bacteria that work well within a human or animal body may decrease in number, an event which allows harmful competitors to thrive. A specific example of microbe that may be present in a probiotic is lactic acid bacteria (LAB). LAB have been used in the food industry for many years, because they are able to convert sugars (including lactose) and other carbohydrates into lactic acid. Strains of the genera *Lactobacillus* and *Bifidobacterium*, are the most widely used probiotic bacteria. A dosage form according to the present description, in the form of a "probiotic dosage form" can include one or more probiotic material such as a live bacteria or yeast, in combination with an amount of theanine as described herein.

A dosage form may be a "prebiotic dosage form," which is a dosage form that contains theanine in combination with a "prebiotic material," which is a nondigestible food ingredient that beneficially affects a host by selectively stimulating the growth or activity of one or a limited number of bacteria in the colon. A prebiotic material may be a selectively fermented ingredient that allows specific changes in the composition or activity in the gastroesophageal microflora, that confers benefits upon host well-being and health. Typically, prebiotic materials include carbohydrates (such as oligosaccharides), but the definition does not preclude non-carbohydrates. The most prevalent forms of prebiotic materials are nutritionally classed as soluble fiber. Examples of dietary nondigestible oligosaccharides that are considered to be "prebiotic materials" include fructooligosaccharides and galactooligosaccharides. Thus, a prebiotic dosage form according to this description can include a prebiotic material in combination with theanine being present in an amount as described herein.

A single example of a dosage form that is considered to be a "dietary supplement" may be in the form of a dosage form useful to treat GERT or heartburn, in the form of a pill or a beverage (or a precursor, such a powder or concentrate that would be combined with a liquid to form a beverage). The pill or beverage includes fiber (soluble fiber, insoluble fiber, or both) to improve gastric emptying, e.g., in an amount in the range from 7 to 14 grams fiber. The pill or beverage also includes theanine in an amount in the range from 50 to 200 mg, e.g., from 50 to 100 mg.

An example of a dosage form that is considered to be a "medical food" may be in the form of a liquid composition that approximately contains nutrition and calories of a single meal. This type of dosage form can be useful to treat GERT, particularly patients having severe GERT symptoms. The liquid includes components of a meal including fiber, protein, fat, carbohydrates, and micronutrients, in amounts sufficient to supply from 15 to 40 percent of minimum recommended dietary allowances (from the US Food and Drug Administration), e.g., from 20 to 35 percent of the recommended dietary allowance. For an adult, these recommended dietary allowances include: 65 grams per day fat, 300 grams per day total carbohydrates, 25 grams per day fiber, 50 grams per day protein, 60 mg Vitamin C, 1000 mg calcium, 18 mg iron, 5000 IU Vitamin A, 400 IU Vitamin D, and others. An embodiment of a medical food according to the invention may contain a portion of any combination of these materials, and will also include theanine in an amount in the range from 50 to 200 mg, e.g., from 50 to 100 mg. Optionally this embodiment of medical food dosage form can also include a total amount of food calories in the range from 150 to 300 food energy calories (i.e. kilogram calories, in that the context of food energy the term calorie generally refers to the kilogram calorie), e.g., from 170 to 200 food energy calories (kilocalories).

Yet another embodiment of a particular dosage form is a serving of yogurt that contains theanine in an effective amount as described. A serving of yogurt may be from 6 to 16 fluid ounces, e.g., from 7 to 13 fluid ounces, and may contain from 50 to 200 mg theanine, or from 100 to 200 mg theanine.

Yet another example of a dosage form is a liquid beverage, as described, including. The liquid beverage may contain with any one or more of nutrients, fiber, carbohydrates, protein, etc. A container or a serving of the liquid beverage may be from 6 to 48 fluid ounces, e.g., from 8 to 32 fluid ounces, and may contain from 50 to 200 mg theanine, or from 100 to 200 mg theanine.

Useful dosage forms can be prepared by methods and techniques that will be well understood by those of skill in the vitamin arts and may include the use of additional ingredients in producing tablets, capsules, or liquid dosage forms, food products, and the like.

The invention claimed is:

1. A method of treating a patient who has gastroesophageal reflux disease (GERD), the method comprising orally administering theanine in a gastroesophageal reflux inhibiting amount, wherein a symptom of gastroesophageal reflux is thereby prevented or reduced, and thereby treating the GERD.

2. The method according to claim 1 wherein the theanine is administered at a dosage in the range of 50 to 200 milligrams and from 2 to 4 hours prior to ingestion of food or a liquid beverage.

3. The method according to claim 1 wherein the theanine is administered in a prebiotic dosage form, a probiotic dosage form, a solution or a liquid dosage form.

4. The method according to claim 3 wherein the probiotic dosage form comprises yogurt.

5. The method according to claim 1 comprising orally administering the theanine at a dosage in the range of 50 to 600 milligrams per day.

6. The method according to claim 1 comprising orally administering the theanine at a dosage in the range of 300 to 600 milligrams per day.

7. The method according to claim 1 comprising orally administering the theanine as three dosages of theanine in a day, each dosage at a dosage in the range of 50 to 200 milligrams to effect a total dosage in the range of 150 to 600 milligrams.

8. The method according to claim 1 comprising orally administering the theanine at a regular dosage for at least two days.

9. The method according to claim 1 comprising orally administering the theanine at a regular dosage for at least two weeks.

10. The method according to claim 1 comprising orally administering the theanine at a regular dosage for at least two weeks, then administering theanine at a reduced dosage.

11. The method according to claim 1 comprising orally administering the theanine at a supplemental dosage in the range of 20 to 200 milligrams, within an hour prior to a precipitating factor for gastroesophageal reflux.

12. The method according to claim 11 wherein the precipitating factor is selected from ingestion of food, a food product, recumbency, and combinations thereof.

13. The method according to claim 12 wherein the precipitating factor is recumbency for overnight sleep or the precipitating factor comprises chocolate or coffee.

14. The method according to claim 1, wherein the symptom comprises heartburn.

15. The method according to claim 1, wherein the theanine is administered in a solid dosage form.

16. A method of treating a patient who has gastroesophageal reflux disease (GERD), the method comprising orally administering theanine in a gastroesophageal reflux inhibiting amount within an hour prior to a precipitating factor for gastroesophageal reflux, wherein a symptom of gastroesophageal reflux is thereby prevented or reduced, and thereby treating the GERD.

17. The method according to claim 16 wherein the precipitating factor is selected from ingestion of food, a food product, recumbency, and combinations thereof.

18. The method according to claim 17 wherein the precipitating factor is recumbency for overnight sleep or the precipitating factor comprises chocolate or coffee.

19. The method according to claim 16, wherein the symptom comprises heartburn.

20. The method according to claim 16 comprising orally administering the theanine at a dosage in the range of 50 to 200 milligrams, within an hour prior to a precipitating factor for gastroesophageal reflux.

21. The method according to claim 20 wherein the theanine is administered at a dosage in the range of 100 to 200 milligrams, within an hour prior to a precipitating factor for gastroesophageal reflux.

* * * * *